US010059948B2

(12) United States Patent
 Waterworth

(10) Patent No.: US 10,059,948 B2
(45) Date of Patent: Aug. 28, 2018

(54) ANTISENSE TREATMENT OF RADIATION INDUCED DISEASES IN THE GASTROINTESTINAL TRACT

(71) Applicant: Atlantic Pharmaceuticals (Holdings) Ltd, Saffron Walden Essex (GB)

(72) Inventor: Toby Wilson Waterworth, Saffron Walden (GB)

(73) Assignee: Atlantic Pharmaceuticals (Holdings) Ltd., Saffron Walden Essex (GB)

( * ) Notice: Subject to any disclaimer, the term of this patent is extended or adjusted under 35 U.S.C. 154(b) by 0 days.

(21) Appl. No.: 15/308,352

(22) PCT Filed: May 1, 2015

(86) PCT No.: PCT/GB2015/051277
§ 371 (c)(1),
(2) Date: Nov. 1, 2016

(87) PCT Pub. No.: WO2015/166263
PCT Pub. Date: Nov. 5, 2015

(65) Prior Publication Data
US 2017/0067062 A1    Mar. 9, 2017

(30) Foreign Application Priority Data

May 2, 2014   (GB) .................................. 1407822.4

(51) Int. Cl.
| | | |
|---|---|---|
| A61K 31/70 | (2006.01) | |
| C07H 21/02 | (2006.01) | |
| C07H 21/04 | (2006.01) | |
| C12N 15/113 | (2010.01) | |
| A61K 31/711 | (2006.01) | |

(52) U.S. Cl.
CPC ........ *C12N 15/1138* (2013.01); *A61K 31/711* (2013.01); *C12N 2310/11* (2013.01); *C12N 2310/315* (2013.01)

(58) Field of Classification Search
None
See application file for complete search history.

(56) References Cited

U.S. PATENT DOCUMENTS

| | | |
|---|---|---|
| 6,096,722 A | 8/2000 | Bennett et al. |
| 6,747,014 B2 | 6/2004 | Teng et al. |
| 2009/0275631 A1* | 11/2009 | Wedel ................ C12N 15/1138 514/44 A |

FOREIGN PATENT DOCUMENTS

| | | |
|---|---|---|
| WO | WO 03/052121 A2 | 6/2003 |
| WO | WO 2010/006237 A2 | 1/2010 |

OTHER PUBLICATIONS

Kountoras et al . World J Gastroenerol vol. 14(48):7289-7301, 2008.*
Miner et al., "Bioavailability and therapeutic activity of alicaforsen (ISIS 2302) administered as a rectal retention enema to subjects with active ulcerative colitis", Alimentary Pharmacology & Therapeutics, vol. 23, No. 10, May 1, 2006, pp. 1427-1434.
Dustin et al., "Induction by IL 1 and Interferon—$\gamma$: Tissue Distribution, Biochemistry, and Function of a Natural Adherence Molecule (ICAM-1)", *J. Immunol* , 137:245-54, 1986.
Rothlein et al., "A Human Intercellular Adhesion Molecule (ICAM-1) Distinct From LFA-1", *J. Immunol* , 137:1270-4, 1986.
Simmons et al., "ICAM, an adhesion ligand of LFA-1, is homologous to the neural cell adhesion molecule NCAM", *Nature* , 331:624-7, 1988.
Ausubel et al., "Current Protocols in Molecular Biology", Wiley Interscience Publishers, (1995).
Sambrook et al., "Molecular Cloning: A Laboratory Manual", $2^{nd}$ edition, col. 1, pp. 1.101-104, pp. 9.47-9.62; New York: Cold Spring Harbor Laboratory Press, 1989.
Geary et al., "Antisense oligonucleotide inhibitors for the treatment of cancer: 1. Pharmacokinetic properties of phosphorothioate oligodeoxynucleotides", Anti-Cancer Drug Design, 12:383-94, 1997.
Butler et al., "Cellular Distribution of Phosphorothioate Oligodeoxynucleotides in Normal Rodent Tissues", *Lab. Invest* , 77:379-88.
Mirabelli et al., "In vitro and in vivo pharmacologic activities of antisense oligonucleotids", Anti-Cancer Drug Des., 6:647-61, 1991.

* cited by examiner

*Primary Examiner* — Sean McGarry
(74) *Attorney, Agent, or Firm* — Knobbe, Martens, Olson & Bear, LLP

(57) ABSTRACT

This invention relates to a composition comprising an antisense oligonucleotide for use in treating radiation induced disease of the gastrointestinal tract.

17 Claims, No Drawings

ANTISENSE TREATMENT OF RADIATION INDUCED DISEASES IN THE GASTROINTESTINAL TRACT

CROSS-REFERENCE TO RELATED APPLICATIONS

This application is a U.S. National Phase under 35 U.S.C. § 371 of International Application No. PCT/GB2015/051277, filed May 1, 2015, which claims priority to Great Britain Patent Application No. 1407822.4, filed May 2, 2014, each of which is hereby incorporated by reference in its entirety into this application.

This invention relates to a composition comprising an antisense oligonucleotide for use in treating radiation induced disease of the GI tract.

Radiation therapy can be highly effective in the treatment of cancers in the pelvic area, such as pelvic tumours. There are currently around 17,000 patients treated annually with pelvic radiation in the UK alone. A side effect for people who have had radiation therapy that targets the pelvic area is Radiation Induced Proctitis for which there is no approved therapy and a major unmet medical need.

Radiation Induced Proctitis can cause persistent and/or severe bleeding, accompanied by rectal discharge and diarrhea, long term fibrosis and stenosis related complications requiring surgery and all affecting quality of life. Thermal therapy may be used to stop bleeding and inflammation. Thermal therapy targets the rectal lining with a heat probe, electric current, or laser. In many cases, several treatments are required. Such therapy is invasive and is generally considered unpleasant to the patient, with concerns regarding patient compliance. Sucralfate, 5-aminosalicyclic acid (5-ASA) or corticosteroid enemas can also be used to ease pain and reduce inflammation from radiation proctitis, although their effectiveness is limited.

An ICAM-1 antisense oligonucleotide comprising the nucleic acid sequence of SEQ ID NO: 1 has previously been used to treat ulcerative colitis (UC) and pouchitis, both of which are auto-immune diseases. Radiation Induced Proctitis is not such a disease.

ICAM-1, a member of the immunoglobulin (Ig) superfamily, is an inducible transmembrane glycoprotein constitutively expressed at low levels on vascular endothelial cells and on a subset of leucocytes (Dustin et al., *J. Immunol*, 137:245-54, 1986; Rothlein et al, *J. Immunol.*, 137:1270-4, 1986; Simmons et al, *Nature,* 331:624-7, 1988). SEQ ID NO:1 is a 20-base phosphorothioate oligodeoxynucleotide designed to specifically hybridize to a sequence in the 3'-untranslated region of the human ICAM-1 mRNA.

It has been determined that a composition comprising an oligonucleotide having a sequence comprising SEQ ID NO: 1 is extremely effective for treating Radiation Induced Proctitis. Treatment of Radiation Induced Proctitis includes the delay, reduction and/or amelioration of any symptom of Radiation Induced Proctitis, including rectal bleeding, bloody bowel movements, a feeling of rectal fullness, and/or rectal pain, crampy abdominal pain, rectal discharge of mucus or pus and/or diarrhoea or frequent passage of loose or liquid stools.

According to a first aspect of the invention, there is provided a composition comprising an oligonucleotide comprising the nucleic acid sequence of SEQ ID NO:1 for use in radiation induced disease of the GI tract.

SEQ ID NO:1 is as follows: 5'-gcccaagctg gcatccgtca-3'

In one embodiment, the composition comprises an oligonucleotide consisting of the nucleic acid sequence of SEQ ID NO:1.

The oligonucleotides in accordance with this invention preferably comprise from about 20 to about 80 nucleic acid base units. It is more preferred that such oligonucleotides comprise from about 20 to 50 nucleic acid base units, still more preferred to have from about 20 to 30 nucleic acid base units, and most preferred to have from about 20 to 22 nucleic acid base units. As will be appreciated, a nucleic acid base unit is a base-sugar combination suitably bound to an adjacent nucleic acid base unit through phosphodiester or other bonds. One skilled in the art will understand that about 20 to about 80 nucleic acid base units includes 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleobase units.

In a further embodiment, the composition comprises a fragment of SEQ ID NO:1, wherein the fragment is at least 8, 9, 10, 11, 12, 13, 14, 15, 16, 17, 18 or 19 nucleotides in length. The fragment can hybridise to a sequence in the 3'-untranslated region of the human ICAM-1 mRNA. The fragment can hybridise under moderate or stringent conditions with nucleotides 'cctgacg gatgccagct tgg' (SEQ ID NO:2). Fragments include 'cccaagctg gcatccgtca' (SEQ ID NO:3), 'gcccaagctg gcatccgtc' (SEQ ID NO:4) and 'gcccaagctg gca' (SEQ ID NO:5).

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

As herein defined, "Stringent conditions" or "highly stringent conditions", may be identified by those that: (1) employ low ionic strength and high temperature for washing, for example 0.015 M sodium chloride/0.0015 M sodium citrate/0.1% sodium dodecyl sulphate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 [mu]g/ml), 0.1% SDS, and 10% dextran sulphate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulphate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

As used herein, conditions of moderate or high stringency can be readily determined by those having ordinary skill in the art based on, for example, the length of the DNA. The basic conditions are set forth by Sambrook et al. Molecular Cloning: A Laboratory Manual, 2 ed. Vol. 1, pp. 1.101-104, Cold Spring Harbor Laboratory Press, (1989).

The oligonucleotide can be modified to comprise at least one phosphorothioate linkage. Phosphorothioate modification of the oligonucleotide, by substituting a sulfur molecule for a non-bridging oxygen molecule in each phosphodiester linkage, significantly increases exonuclease resistance relative to unmodified DNA and prolongs the drug half life (Geary et al., Anti-Cancer Drug Design, 12:383-94, 1997). Phosphorothioate oligonucleotides are only minimally antigenic, non-cytotoxic and well tolerated, and their pharmacokinetic and pharmacodynamic properties are well characterized (see e.g., Butler et al., Lab. Invest, 77:379-88, 1997; Mirabelli et al., Anti-Cancer Drug Des., 6:647-61, 1991).

In addition to phosphorothioate backbone modifications, a number of other possible backbone, sugar and other modifications are well known to those skilled in the art.

The composition is for use in association with any radiation therapy which may result in Radiation Induced Colitis and other radiation induced diseases of the GI tract. Radiation induced disease of the GI tract includes Radiation Induced Colitis or any other radiation induced disease of the GI tract following radiation treatment for pelvic tumours, prostate cancer, ovarian cancer, skin cancer, bowel cancer as well as cancer of the bladder, pelvis, cervix, colorectal, testis and head and neck; wherein the cancer is primary and/or metastatic.

The use of the composition of the present invention is specifically to address the side effect of proctitis when caused by radiation therapy.

The use of the composition may be at any time in association with the radiation therapy. For example, the composition may be administered before and/or during and/or after the radiation therapy.

The composition can be formulated for rectal, oral and parenteral administration. Compositions for rectal administration include solutions, such as enemas and suppositories, and emulsions or foams. Absorption promoting adjuvants can be included with the composition. Compositions for oral administration include tablets, all liquids, gels, syrups, enteric coated capsules and colonic enteric-coated capsules.

Formulations for the rectal delivery of pharmaceutical compositions are well known to those skilled in the art. The selection of a specific formulation is based on considerations well known to those skilled in the art. Detailed formulations are presented in U.S. Pat. Nos. 6,096,722 and 6,747,014 both incorporated herein by reference.

The composition comprising an oligonucleotide comprising the nucleic acid sequence of SEQ ID NO:1 may be administered alone but can also be combined with another pharmaceutical agent.

A composition according to the invention preferably contains ISIS 2302, hydroxypropyl methylcellulose, methylparaben sodium, propylparaben sodium, monobasic sodium phosphate monohydrate and/or water.

A composition according to the invention preferably contains ISIS 2302, dibasic sodium phosphate, monobasic sodium phosphate, sodium chloride, sodium hydroxide, hydrochloric acid and/or water.

In a preferred embodiment, the subject is human.

The precise dose of the oligonucleotide will depend upon a number of factors, including the severity of the inflammation, pain and/or discharge. The composition is preferably administered to an individual in a "therapeutically effective amount", this being sufficient to show benefit to the individual.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

For example, in one embodiment, a suitable dose may be 60 ml/240 mg, 70 ml/240 mg, 80 ml/240 mg, 90 ml/240 mg, 100 ml/240 mg, 30 ml/120 mg, 60 ml/120 mg, 70 ml/120 mg, 80 ml/120 mg, 90 ml/120 mg, 100 ml/120 mg per dose, for example, per enema.

The composition may be administered once, twice, three or four times a day or periodically.

The composition can be administered for 3, 4, 5, 6, 7, 8 or more weeks. A peak response is achieved 8, 9, 10, 11, 12 weeks or more after the treatment commences.

The patient can be in remission of symptoms for 4-12, 6-12, 6-18 or more including 16-36 months after treatment.

An administration regime in combination with the radiation therapy may be: before, during or after radiation therapy. Radiation therapies include conventional 2-dimensional radiation therapy, 3-dimensional conformal radiation therapy, intensity-modulated radiation therapy, brachytherapy (low or high dynamic range), stereotactic body radiation therapy and proton therapy.

Treatment may include curative, alleviation or prophylactic effects.

More specifically, treatment includes "therapeutic" and "prophylactic" and these types of treatment are to be considered in their broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Prophylactic" also includes preventing reoccurrence of a particular condition in a patient previously diagnosed with the condition. "Therapeutic" may also reduce the severity of an existing condition.

According to a second aspect of the invention, there is provided a method of treating radiation induced disease of the GI tract, comprising administering a composition comprising an oligonucleotide comprising the nucleic acid sequence of SEQ ID NO:1 to the subject.

In one embodiment, the subject is in need of such treatment or can benefit from such treatment.

A therapeutically effective amount of the oligonucleotide is administered to the subject.

The term "therapeutically effective amount" as used herein in the context of treating radiation induced disease of the GI tract means an amount capable of reducing inflammation, pain and/or discharge relative to the inflammation, pain and/or discharge experienced by the subject before the composition of the invention is administered.

The term 'treatment' is used herein to refer to any regimen that can benefit a human.

Preferred features for the second and subsequent aspects of the invention are as for the first aspect mutatis mutandis.

The invention will now be further described by way of reference to the following Example, which is provided for the purposes of illustration only and are not to be construed as being limiting on the invention.

EXAMPLE 1

Analysis of Single High Dose of Radiotherapy and ISIS 2302 Treatment in Rats.

In order to induce proctitis in rats radiation is administered to the rat abdomen. Rats are shielded by lead with the exception of a 3 cm×4 cm area to the lower pelvis. Irradiation is targeted to the rectum at a rate of 1 Gy/minute. On day 1 one dose of 20 Gy radiation is administered to the rats. Prior to irradiation rats are anaesthetised (ketamine 100 mg/kg, xylazine 5 mg/kg ip) and the animals are treated in a gentle head down position to allow gravity to move other abdominal organs out of the way of the radiation path. Rats are treated for 10 consecutive days via intra-rectal administration of ISIS 2302 or a vehicle control at 0.1 ml/100 g body weight. Table 1 outlines the treatment groups.

TABLE 1

| Group | Radiation Treatment | ISIS 2302 Treatment |
|---|---|---|
| Group 1 | vehicle control (no irradiation) (n = 5) | — |
| Group 2 | vehicle (20 Gy) (n = 10) | — |
| Group 3 | dose group 1 (20 Gy) (n = 10) | commence dosing prior to radiation |
| Group 4 | dose group 2 (20 Gy) (n = 10) | commence dosing concomitant with radiation |
| Group 5 | dose group 3 (20 Gy) (n = 10) | commence dosing after radiation |

Clinical assessment and endoscopy are performed and recorded daily to assess body weight, survival, diarrhoea and blood in the stool. On days 7 and 10 each animal undergoes video endoscopy, under isofluorine anaesthesia and still images are captured. Proctitis is scored and a histological examination is performed post sacrifice of the rats.

EXAMPLE 2

Analysis of Varying Doses of Multifraction Radiation and ISIS 2302 Treatment in Rats.

A similar study to Example 1 is performed with the radiation delivered in 8 fractions of 6 Gy each on days 1-4 and 7-10 with an extended repeat-dosing and follow-up/observation phase. Provision is made for 1-24 days of consecutive dosing with 3 endoscopy evaluations potentially at days 11, 18 and 25.

EXAMPLE 3

Analysis of the Safety and Efficacy of ISIS 2302 Enema in the Treatment of Radiation Induced Proctitis in Humans.

Patients with cancer receiving radical radiotherapy to the pelvis are recruited to a phase 1/2 clinical study. Patients are treated with ISIS 2302 post-surgery (if applicable) but prior to radiotherapy and treatment continues throughout radiotherapy treatment. Radiotherapy commences on study day 1. ISIS 2302 is administered once daily as an enema containing 240 mg of drug. Safety is evaluated on an ongoing basis from randomisation to week 8. Evaluation of efficacy is made at 8 weeks (acute phase; post-radiotherapy). A long-term post-study follow-up is conducted at 1 year to evaluate occurrence of chronic/delayed symptoms.

Primary Outcome Measures:

Proportion of patients which develop radiation proctitis (measured at 8 weeks). Assessed by: endoscopic evaluation; symptoms (pain, rectal bleeding etc); radiotherapy compliance (requirement to miss/adjust doses, consequent to proctitis); requirement for rescue medication.

Secondary Outcome Measures:

Time to occurrence of acute radiation proctitis (measured within 8 week "acute" setting).

Time to occurrence of chronic radiation proctitis (assessed at 1 year time-point). Adverse Events (measured within 8 week "acute" setting).

The invention claimed is:

1. A method of treating radiation induced disease of the GI tract in a subject, comprising administering a composition comprising an oligonucleotide comprising the nucleic acid sequence of SEQ ID NO:1 to the subject.

2. The method of claim 1, wherein the radiation induced disease of the GI tract is Radiation Induced Colitis or any other radiation induced disease of the GI tract following radiation treatment for pelvic tumours, prostate cancer, ovarian cancer, skin cancer, bowel cancer as well as cancer of the bladder, pelvis, cervix, colorectal, testis and head and neck; wherein the cancer is primary and/or metastatic.

3. The method of claim 1 or 2, wherein the composition is formulated for rectal administration.

4. The method of claim 1 or 2, wherein the composition is formulated for oral, parenteral or topical administration.

5. The method of claim 1 or 2, wherein the composition treats mucosal and/or blood discharge.

6. The method of claim 1 or 2, wherein the oligonucleotide comprises at least one phosphorothioate linkage.

7. The method of claim 1 or 2, wherein the composition is administered in combination with oral, parenteral or topical medication.

8. The method of claim 1 or 2, wherein the composition is administered before and/or during radiation therapy.

9. The method of claim 3, wherein the composition treats mucosal and/or blood discharge.

10. The method of claim 4, wherein the composition treats mucosal and/or blood discharge.

11. The method of claim 3, wherein the oligonucleotide comprises at least one phosphorothioate linkage.

12. The method of claim 4, wherein the oligonucleotide comprises at least one phosphorothioate linkage.

13. The method of claim 5, wherein the oligonucleotide comprises at least one phosphorothioate linkage.

14. The method of claim 3, wherein the composition is administered in combination with oral, parenteral or topical medication.

15. The method of claim 3, wherein the composition is administered before and/or during radiation therapy.

16. The method of claim 4, wherein the composition is administered before and/or during radiation therapy.

17. A method of treating radiation induced colitis or proctitis in a human subject, comprising rectally administering a composition comprising an oligonucleotide having a nucleic acid sequence consisting of the nucleic acid sequence of SEQ ID NO:1 to a subject in need of treatment for radiation induced colitis or proctitis prior to and during radiotherapy treatment, wherein the composition is formulated as an enema and wherein the oligonucleotide comprises at least one phosphorothioate linkage.

* * * * *